US010898389B2

(12) United States Patent
Goubard

(10) Patent No.: US 10,898,389 B2
(45) Date of Patent: Jan. 26, 2021

(54) BREATHABLE SELF-ADHESIVE ARTICLES

(75) Inventor: David Goubard, Compiegne (FR)

(73) Assignee: BOSTIK SA, Colombes (FR)

(*) Notice: Subject to any disclaimer, the term of this patent is extended or adjusted under 35 U.S.C. 154(b) by 1031 days.

(21) Appl. No.: 14/384,862

(22) PCT Filed: Mar. 12, 2012

(86) PCT No.: PCT/IB2012/000603
§ 371 (c)(1),
(2), (4) Date: Sep. 12, 2014

(87) PCT Pub. No.: WO2013/136108
PCT Pub. Date: Sep. 19, 2013

(65) Prior Publication Data
US 2015/0030848 A1 Jan. 29, 2015

(51) Int. Cl.
A61F 13/02 (2006.01)
C09J 175/04 (2006.01)
A61L 15/58 (2006.01)
A61L 15/42 (2006.01)
C08G 18/48 (2006.01)
C08G 18/10 (2006.01)
C08G 18/12 (2006.01)
C08G 18/75 (2006.01)
C09J 171/02 (2006.01)
C08G 65/336 (2006.01)
C09J 7/21 (2018.01)
C09J 7/38 (2018.01)
C09J 171/00 (2006.01)
C09J 175/08 (2006.01)
A61F 13/00 (2006.01)

(52) U.S. Cl.
CPC .......... A61F 13/0253 (2013.01); A61L 15/42 (2013.01); A61L 15/58 (2013.01); A61L 15/585 (2013.01); C08G 18/10 (2013.01); C08G 18/12 (2013.01); C08G 18/48 (2013.01); C08G 18/4825 (2013.01); C08G 18/4866 (2013.01); C08G 18/755 (2013.01); C08G 65/336 (2013.01); C09J 7/21 (2018.01); C09J 7/38 (2018.01); C09J 171/00 (2013.01); C09J 171/02 (2013.01); C09J 175/04 (2013.01); C09J 175/08 (2013.01); A61F 2013/00268 (2013.01); C09J 2301/312 (2020.08); C09J 2400/263 (2013.01); C09J 2453/003 (2013.01); C09J 2471/003 (2013.01); C09J 2475/00 (2013.01); C09J 2475/003 (2013.01); Y10T 428/273 (2015.01); Y10T 428/2852 (2015.01)

(58) Field of Classification Search
None
See application file for complete search history.

(56) References Cited

U.S. PATENT DOCUMENTS

| 4,463,115 | A | 7/1984 | Hirose et al. |
| 5,530,063 | A | 6/1996 | Nagai et al. |
| 7,317,051 | B2 | 1/2008 | Georgeau et al. |
| 7,671,144 | B2 | 3/2010 | Fujimoto et al. |
| 8,691,909 | B2 | 4/2014 | Laferte et al. |
| 2005/0107499 | A1 | 5/2005 | Georgeau et al. |
| 2005/0182186 | A1 | 8/2005 | Gielens et al. |
| 2007/0167584 | A1 | 7/2007 | Fujimoto et al. |
| 2008/0058492 | A1* | 3/2008 | Griswold ............ C08G 18/289 528/60 |
| 2010/0286582 | A1* | 11/2010 | Simpson ............... A61F 13/022 602/43 |
| 2011/0052912 | A1 | 3/2011 | Poivet et al. |
| 2011/0151253 | A1 | 6/2011 | Laferte et al. |
| 2011/0154772 | A1 | 6/2011 | Lontchar et al. |

FOREIGN PATENT DOCUMENTS

| EP | 0106330 A1 | 4/1984 |
| EP | 1 431 363 A2 | 6/2004 |
| EP | 1544254 A1 | 6/2005 |
| EP | 1715015 A1 | 10/2006 |
| EP | 1724321 A1 | 11/2006 |
| EP | 2336208 A1 | 6/2011 |
| JP | 05247429 A1 | 9/1993 |
| JP | H07003159 A1 | 1/1995 |
| JP | 2006325675 A1 | 7/2006 |
| WO | 01/42384 A2 | 6/2001 |
| WO | WO2009/106699 * | 9/2009 ............ C09J 175/08 |
| WO | 2011082327 A1 | 7/2011 |

OTHER PUBLICATIONS

International Search Report for PCT/IB2012/000603 dated Jan. 31, 2013.
English Abstract of EP1724321, Publication Date: Nov. 22, 2006.
English Abstract and Machine Translation of Claims for JP2006-325675, Publication Date: Dec. 7, 2006.
English Abstract and Machine Translation of Claims for JP05-247429, Publication Date: Sep. 24, 1993.

* cited by examiner

Primary Examiner — Scott R. Walshon
Assistant Examiner — Elaine M Vazquez
(74) Attorney, Agent, or Firm — Millen, White, Zelano and Branigan, P.C.

(57) ABSTRACT

The invention relates to the use of an adhesive composition comprising at least one silyl-containing polymer, at least one compatible tackifying resin and at least one catalyst, to make a breathable self-adhesive article. The invention also relates to a breathable self-adhesive article comprising at least one breathable substrate coated with a breathable adhesive layer. The invention also relates to a pressure-sensitive adhesive composition.

18 Claims, No Drawings

BREATHABLE SELF-ADHESIVE ARTICLES

FIELD OF THE INVENTION

The invention relates to the use of an adhesive composition to make a breathable self-adhesive article. The invention also relates to a breathable self-adhesive article comprising at least one breathable substrate coated with a breathable adhesive layer. The invention also relates to a pressure-sensitive adhesive composition.

BACKGROUND OF THE INVENTION

Pressure-Sensitive Adhesives or PSAs are substances that give the support, also called carrier, coated therewith an immediate tack at room temperature, which allows its instantaneous adhesion to an article under the effect of brief slight pressure.

Generally, PSAs are based on adhesive compositions in a solvent phase. Those solvents aim at improving mixing, dosing or pumping of those adhesives during their production but also at facilitating their coating in thin layer, which after solvent evaporation will be a self-adhesive layer. Nevertheless, the use of solvents is subjected to stricter and stricter regulations.

More recently, water-based adhesives have been developed. In this case, the problems related to solvents are solved but a problem related to the evaporation step persists. Indeed, the energy necessary to evaporate water from the coated adhesive composition is very high; thus, the process is not satisfying with regards to energy demand, therefore it is dissatisfying from an environmental point of view.

Even more recently, adhesives based on solvent-free technologies have been developed. Those adhesives are named "Hot-Melt Pressure-Sensitive Adhesives" (HMPSA). HMPSAs generally comprise a thermoplastic polymer, in particular elastomeric block copolymers, usually in combination with tackifying resins and plasticizers.

Breathable self-adhesive articles can be used in medical applications such as bandage, blisters, wound dressing, electrode pads, plasters, in clothing applications such as breathable clothing for dealing with wet weather or breathable dry clothing exposed to wet environment, and in building applications such as roofing or wall covering, or window frame water-proof systems that still need to be breathable for humidity to get released to environment.

Adhesive materials for example used in medical field such as medical tapes, wound care dressings, and consumer bandages need a high Moisture Vapor Transmission Rate (MVTR) to allow the escape of moisture generated by the skin or by wound exudate. A high MVTR of the adhesive product prevents moisture from being trapped under the dressing, which could otherwise cause maceration of the skin. Sometimes the adhesive material is not breathable enough (i.e., has a MVTR value which is too low), and still is part of a breathable self-adhesive article as it is coated in a form of a discrete pattern: the coating application process is made in a way that adhesive covers some parts of the surface area, and some other parts are not covered: fiber spray coating, or comb-slot coatings are examples where there are open areas left between adhesive fibers, or between adhesive lines, with dimensions of several micrometers to several millimeters.

The adhesive composition has also to be safe for an application on human skin.

Document WO 01/42384 describes water vapor permeable pressure-sensitive adhesives comprising a copolymer having an MVTR of at least 1900 g/m$^2$/24 h and comprising acrylate monomers eventually in mixture with (meth)acrylic acid. The PSA described in this document is a solvent-based pressure-sensitive adhesive.

Document EP 1 431 363 describes hot-melt adhesives based on acrylic block copolymers. In this document adhesive testing is exhibited only at room temperature, and therefore there is a limitation of testing shear resistance of such HMPSA compositions at temperature exceeding 70 or 90° C. Such test conditions at high temperature would show that such adhesives cannot be used in all applications where conditions like severe weather conditions require the adhesive to perform well over time. If acceptable shear resistance (more than 10 minutes at 90° C.) could be reached, then adhesive performances like loop tack would be very poor (less than 0.79 N/cm according to our test conditions).

Document WO 2009/106699 describes a heat-cross-linkable adhesive composition based on a polyurethane comprising two alkoxysilane-type end groups.

Document EP 2 336 208 describes a heat-cross-linkable adhesive composition, said composition being based on a polyether comprising two hydrolysable alkoxysilane-type end groups.

Documents WO 2009/106699 and EP 2 336 208 do not mention or suggest that breathable adhesive layers can be obtained from such compositions.

SUMMARY OF THE INVENTION

A first object of the present invention is the use of an adhesive composition comprising at least one silyl-containing polymer, at least one tackifying resin and at least one catalyst, to make a breathable self-adhesive article According to one embodiment, the adhesive article comprises a substrate and an adhesive layer.

According to one embodiment, the adhesive composition comprises:

a) from 20 to 85% by weight, preferably from 30 to 75% by weight of at least one silyl-containing polymer, b) from 15 to 80% by weight, preferably from 25 to 70% by weight of at least one tackifying resin, c) from 0.01 to 3% by weight, preferably from 0.1 to 2% by weight of at least one catalyst.

According to one embodiment, the tackifying resin has a Softening Point inferior or equal to 150° C., preferably inferior or equal to 130° C., more preferably inferior or equal to 120° C.

According to one embodiment, the silyl-containing polymer is selected from a silyl-containing polyether, a silyl-containing polyurethane, a silyl-containing polyurethane having polyurethane-polyether and polyurethane-polyester blocks, and mixtures thereof.

According to one embodiment, the tackifying resin is selected from phenol modified terpene resins, hydrocarbon resins, rosin ester resins, acrylic resins and mixtures thereof.

According to one embodiment, the adhesive layer having a coating weight below 50 g/m$^2$ has a Moisture-Vapour Transmission Rate superior or equal to 300 g/m$^2$/24 h, preferably superior or equal to 500 g/m$^2$/24 h, more preferably superior or equal to 1000 g/m$^2$/24 h, particularly superior or equal to 2000 g/m$^2$/24 h.

According to one embodiment, the adhesive layer having a coating weight below or equal to 30 g/m$^2$ has a Moisture-Vapour Transmission Rate superior or equal to 500 g/m$^2$/24 h, preferably superior or equal to 750 g/m$^2$/24 h, more preferably superior or equal to 1000 g/m$^2$/24 h.

According to one embodiment, the adhesive layer having a coating weight superior or equal to 50 g/m² has a Moisture-Vapour Transmission Rate superior or equal to 100 g/m²/24 h, preferably superior or equal to 200 g/m²/24 h, more preferably superior or equal to 400 g/m²/24 h, particularly superior or equal to 1000 g/m²/24 h.

According to one embodiment, the substrate has a Moisture-Vapour Transmission Rate superior or equal to the Moisture-Vapour Transmission Rate of the adhesive layer.

Another object of the present invention is a self-adhesive article comprising a substrate having a Moisture-Vapour Transmission Rate superior or equal to 1000 g/m²/24 h, wherein at least one face of said substrate is coated with an adhesive layer obtained by curing an adhesive composition as disclosed in the present invention, said adhesive layer having a Moisture-Vapour Transmission Rate superior or equal to 300 g/m²/24 h for a coating weight below 50 g/m² and a Moisture-Vapour Transmission Rate superior or equal to 100 g/m²/24 h for a coating weight superior or equal to 50 g/m².

According to one embodiment, the adhesive layer having a coating weight below 50 g/m² has a Moisture-Vapour Transmission Rate superior or equal to 500 g/m²/24 h, preferably superior or equal to 1000 g/m²/24 h, particularly superior or equal to 2000 g/m²/24 h.

According to one embodiment, the adhesive layer having a coating weight superior or equal to 50 g/m² has a Moisture-Vapour Transmission Rate superior or equal to 200 g/m²/24 h, preferably superior or equal to 400 g/m²/24 h, particularly superior or equal to 1000 g/m²/24 h.

Another object of the invention is a process for manufacturing the self-adhesive article of the present invention, comprising the steps of:
a) Conditioning an adhesive composition as disclosed in the present invention at a temperature from 20° C. to 160° C., then
b) Coating the adhesive composition obtained at step a) onto a carrying surface; then
c) Curing the coated adhesive composition by heating the coated substrate at a temperature from 20° C. to 200° C.; optionally,
d) Laminating the cured adhesive layer onto a substrate having a Moisture-Vapour Transmission Rate superior or equal to 1000 g/m²/24 h.

According to one embodiment, the curing is carried out in an atmosphere in which from 5 to 100% of the molecules are water molecules, preferably from 10 to 90% of the molecules are water molecules, more preferably from 15 to 70% of the molecules are water molecules.

A further object of the invention is an adhesive composition characterized in that it comprises:
a) at least one silyl-containing polymer,
b) at least one compatible tackifying resin selected from:
copolymers comprising at least (meth)acrylic monomers and hydrocarbon monomers, and:
polymers containing at least one (meth)acrylic function or chain part, and at least one hydrocarbon chain part,
c) at least one catalyst.

According to one embodiment, the tackifying resin is selected from:
a) a mixture of styrene-acrylic resins and rosin ester resins, and
b) a dicyclopentadiene-acrylic polymer.

According to one embodiment, the adhesive composition comprises:
a) from 20 to 85%, preferably from 30 to 75% by weight of at least one silyl-containing polymer, b) from 15 to 80%, preferably from 25 to 70% by weight of at least one tackifying resin,
c) from 0.01 to 3%, preferably from 0.1 to 2% by weight of at least one catalyst.

Further features and advantages of the invention will appear from the following description of embodiments of the invention, given as non-limiting examples, with reference to the accompanying drawings listed hereunder.

DETAILED DESCRIPTION OF THE INVENTION

A first object of the present invention is the use of an adhesive composition comprising at least one silyl-containing polymer, at least one compatible tackifying resin and at least one catalyst, to make a breathable self-adhesive article comprising a substrate and an adhesive layer.

Breathability is defined as the property of a material to let vaporized substances go through its structure, especially when applied in thin coating, from 1 to 5000 g/m². The breathability phenomenon should not significantly transform the structure of the material. Vaporized substances may be water or any gaseous substance at ambient temperature and ambient pressure conditions, whether partial pressure is high or low in air, or any substance vaporized in any gaseous media, naturally or with specific conditions.

The breathability is quantified by the Moisture-Vapor Transmission Rate (MVTR). Herein, MVTR is measured according to EN 13726-2 standard.

According to one embodiment, the adhesive composition comprises:
from 20 to 85% by weight, preferably from 30 to 75% by weight of at least one silyl-containing polymer,
from 15 to 80% by weight, preferably from 25 to 70% by weight of at least one tackifying resin,
from 0.01 to 4% by weight, preferably from 0.1 to 3% by weight of at least one catalyst.

The adhesive composition according to the invention is preferably any hot melt adhesive composition, namely a composition that is applied at temperatures superior or equal to 50° C., preferably superior or equal to 70° C., more preferably superior or equal to 90° C. with no significant quantity of solvent (typically inferior or equal to 5% by weight based on the total weight of the material), has a loop tack representing a PSA behaviour of minimum of 0.79 N/cm after at least partially curing the silylated functions, preferably with no residues, on glass plate. Said adhesive composition comprises at least 5% by weight of an oligomer or a polymer or a large molecule with an average molecular weight ranging from 100 to 250,000 g/mol, preferably from 200 to 80,000 g/mol, more preferably from 500 to 60,000 g/mol and a chemical structure comprising from 0.01 to 4 mol/kg, preferably from 0.1 to 3.5 mol/kg of silylated functions.

Silyl-Containing Polymer

The polymer is a silyl-containing polymer with no significant quantity of solvent, typically inferior or equal to 5% by weight based on the total weight of the material. By "silyl-containing polymer" is meant an oligomer or a polymer or a large molecule with an average molecular weight ranging from 100 to 250,000 g/mol, preferably from 200 to 80,000 g/mol, more preferably from 500 to 60,000 g/mol and having a chemical structure comprising from 0.1 to 4 mol/kg of silylated functions. Said silylated functions can be grafted at the extremities of the polymer or at any part of the polymer chain. By "silylated functions" is meant a function having the following formula (I):

$$-\text{Si}(R^4)_p(OR^5)_{3-p} \qquad (I)$$

wherein:

$R^4$ and $R^5$, which are identical or different, each represent a linear or branched alkyl radical having 1 to 4 carbon atoms, with the possibility, when there are several $R^4$ (or $R^5$) radicals, that these are identical or different, p is an integer equal to 0, 1 or 2.

The molecular weight is measured according methods well-known for one of ordinary skills in the art, such as by Gel-Permeation Chromatography (GPC) using a calibration with Polystyrene Standards.

According to one embodiment, the adhesive composition of the invention is of the type described in documents WO 2009/106699 or EP 2 336 208.

Silyl-Containing Polyurethane (P4) Described in WO 2009/106699

According to one embodiment, the adhesive composition comprises a silyl-containing polyurethane (P4) having the following formula (II):

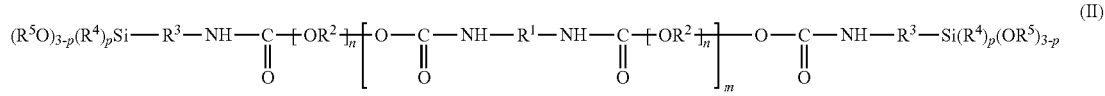

wherein:

$R^1$ represents a hydrocarbon-based divalent radical comprising from 5 to 15 carbon atoms which may be aromatic or aliphatic, linear, branched or cyclic, $R^2$ represents a linear or branched alkylene divalent radical comprising from 1 to 4 carbon atoms, $R^3$ represents a linear alkylene divalent radical comprising from 1 to 3 carbon atoms, $R^4$ and $R^5$, which are identical or different, each represent a linear or branched alkyl radical having 1 to 4 carbon atoms, with the possibility, when there are several $R^4$ (or $R^5$) radicals, that these are identical or different, n is an integer such that the number-average molecular weight of the polyether block of formula $-[OR^2]_n-$ is between 300 Da and 30 kDa, m is an integer such that the number-average molecular weight of the polymer of formula (II) is between 600 Da and 60 kDa;

p is an integer equal to 0, 1 or 2.

Silyl-Containing Polyether (P3) Described in EP 2 336 208

According to another embodiment, the adhesive composition comprises a silyl-containing polyether (P3) having the following formula (III):

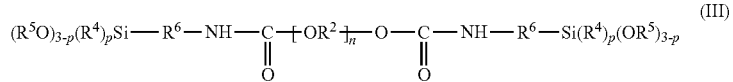

wherein:

$R^2$ represents a linear or branched alkylene divalent radical comprising from 1 to 4 carbon atoms, $R^6$ represents a linear alkylene divalent radical comprising from 1 to 6 carbon atoms, $R^4$ and $R^5$, which are identical or different, each represent a linear or branched alkyl radical having 1 to 4 carbon atoms, with the possibility, when there are several $R^4$ (or $R^5$) radicals, that these are identical or different, n is an integer such that the number average molecular weight of the polymer of formula (III) is between 20 kDa and 40 kDa, p is an integer equal to 0, 1 or 2.

Silyl-Containing Polyurethane (P1)

According to one embodiment, the silyl-containing polymer is a silyl-containing polyurethane (P1) obtained by the following process:

a1) reaction of a mixture of alcohols comprising a polyether polyol (A1) with a stoichiometric excess of diisocyanate (B1), in order to form a polyurethane-polyether block (C1) having at least two terminal —NCO groups; then b1) reaction between the product (C1) obtained at the preceding step with a stoichiometric or a slight excess quantity of an alpha, beta or gamma-aminosilane (D1).

Furthermore, during the second step b1), the aminosilane (D1) reacts, according to a quantitative reaction, with the residual quantity of diisocyanate (C) remaining at the end of the first step a1), in order to form the silane derivative of said isocyanate. Said derivative contributes to the cross-linking reaction of the silyl-containing polymer. Said derivative reacts with the silyl-containing polymer to make three-dimensional network having siloxane links.

Silyl-Containing Polyurethane (P2) Having Polyurethane-Polyether and Polyurethane-Polyester Blocks According to one embodiment, the silyl-containing polymer is a silyl-containing polyurethane (P2) having polyurethane-polyether and polyurethane-polyester blocks, said silyl-containing polyurethane (P2) being obtained by the following process:

a2) reaction of a mixture of alcohols comprising a polyether polyol (A2) with a stoichiometric excess of diisocyanate (B2), in order to form a polyurethane-polyether block (C2) having at least two terminal —NCO groups; then b2) reaction of the polyurethane (C2) obtained at the preceding step with a stoichiometric excess of a polyester polyol (D2), in order to form a polyurethane (E2) having polyurethane-polyether and polyurethane-polyester blocks comprising at least two terminal blocks consisting each in a polyurethane-polyester block having a terminal —OH group; then c2) reaction of the polyurethane (E2), having a terminal —OH group, of the preceding step with a stoichiometric quantity of an isocyanatosilane (F2).

Steps a1) and a2) in the Processes for Manufacturing (P1) and (P2) Respectively

Preferably, the polyether polyols (A1) and (A2) are selected from aliphatic and aromatic polyether polyols. More preferably, their mean molecular mass is ranging from 0.5 to 20 kDa and their hydroxyl functionality is ranging from 2 to 4.6. The hydroxyl functionality is the average number of hydroxyl functions per mole of polyether polyol.

By way of example of aliphatic polyether polyol (A1) and (A2), mention may be made of the oxyalkyl derivatives of:
- diols, such as ethylene glycol, propylene glycol, neopentyl glycol;
- triols, such as glycerol, trimethylolpropane, hexane-1,2, 6-triol;
- tetrols, such as pentaerythritol.

Those products are commercially available.

According to one embodiment, the polyether polyol (A1) or (A2) are selected from polyethers deriving from the condensation of diol monomers or a mixture of polyethers deriving from the condensation of diol monomers with up to 30% by weight of polyethers deriving from the condensation of triol monomers.

According to one embodiment, the polyether polyol (A1) or (A2) is chosen from polypropylene glycols (PPG) having a hydroxyl functionality of 2 or 3, among which, mention may be made of:
- Voranol® EP 1900: difunctional PPG having a molecular weight of about 3800 Da and a hydroxyl index $I_{OH}$ of 28 mg KOH/g;
- Voranol® CP 755: trifunctional PPG having a molecular weight of about 700 Da and a hydroxyl index $I_{OH}$ of 237 mg KOH/g; both available from Dow Company.

According to a preferred embodiment, the polyether polyol (A1) or (A2) is selected from polypropylene glycols having a degree of polymolecularity ranging from 1 to 1.4.

The degree of polymolecularity is the ratio between the weight average molecular mass and the number average molecular weight. Such polypropylene glycols are commercially available from Bayer Company under the trade name ACCLAIM®. By way of example, mention may be made of the trifunctional PPG ACCLAIM® 6300 having a molecular mass of about 6000 Da and an $I_{OH}$ of 28.3 mg KOH/g and of the difunctional PPG:
- ACCLAIM® 8200 N having a number average molecular mass of 8000 Da and an $I_{OH}$ of 13.5 mg KOH/g,
- ACCLAIM® 12200 having a number average molecular mass of 12000 Da and an $I_{OH}$ of 10 mg KOH/g,
- ACCLAIM® 18200 having a number average molecular mass of 18000 Da and an $I_{OH}$ of 6.5 mg KOH/g.

The composition comprising the polyether polyol (A1) or (A2) used in the first step of polymerization a1) or a2) can further comprise one or more chain extenders selected from diols and polyamines having a molecular mass ranging from 60 to 500 Da.

By way of example of such diols, mention may be made of ethylene glycol, propylene glycol, diethylene glycol, dipropylene glycol, 3-methyl-1,5-propanediol, 1,4-butanediol, 1,6-hexanediol, 2-ethyl-1,3-hexanediol, N,N-bis(hydroxyl-2-propyl)aniline, 3-methyl-1,5-pentanediol.

By way of example of such polyamines, mention may be made of ethylene diamine, diphenyl methane diamine, isophorone diamine, hexamethylene diamine, diethyltoluene diamine.

The diisocyanate (B1) or (B2) used in the first step a1) or a2) of the process for making the polyurethane has the formula (IV):

NCO—R$^7$—NCO                 (IV)

wherein R$^7$ represents an aliphatic or aromatic hydrocarbon divalent radical comprising from 5 to 15 carbon atoms, said radical can be linear, branched or cyclic.

According to one embodiment, R$^7$ is chosen from the following divalent radical, the formulas of which show the two free valency:

the divalent radical derived from isophorone:

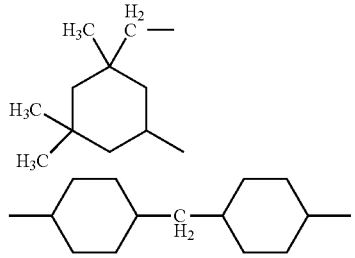

—(CH2)$_6$— (hexamethylene radical)

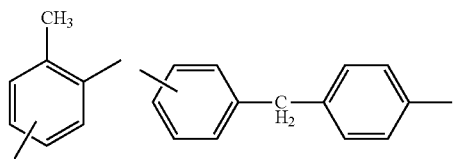

Such diisocyanates are commercially available.

A diisocyanate (B1) or (B2) of formula (IV) wherein R$^7$ is an aliphatic radical is preferred, isophorone diisocyanate (IPDI) is more particularly preferred.

During the first step a1) or a2) of the process, the polyether polyol (A1) or (A2) reacts with an excess of diisocyanate (B1) or (B2) of formula (IV); which means that the quantity of both reactants of step a1) or a2) corresponds to an excess of the equivalent number of —NCO groups (present in the quantity of diisocyanate) in comparison to the equivalent number of —OH groups (present in the quantity of polyether polyol) increased, if appropriate, by the equivalent number of —OH, —NH$_2$, and/or —NH groups present in the diol and/or the diamine used as chain extender.

Preferably, those quantities correspond to an equivalent ratio —NCO/OH ranging from 1.3 to 5. Said ratio is defined as being equal to the equivalent number of —NCO groups divided by the equivalent number of —OH, —NH$_2$, and/or —NH regarding functional groups brought by the corresponding quantities of both reactants, which are the diisocyanate on one hand and the other the mixture of polyether polyols comprising, if appropriate, a chain extender. The quantities by weight of the reactants to be fed into the reactor are determined on the basis of this ratio, as well as, regarding the polyether polyols, on the hydroxyl index $I_{OH}$. The hydroxyl index $I_{OH}$ is the number of hydroxyl functions per gram of polyether polyol, said number being expressed, in particular in the present application, in the form of the equivalent number of milligrams of KOH used in the dosage of hydroxyl functions.

When the diisocyanate (B1) or (B2) is an aliphatic diisocyanate, the step a1) or a2) is preferably carried out in the presence of a catalyst, preferably chosen from organometallic salts such as organometallic salts or complexes of lead, cobalt, iron, nickel, titanium, bismuth, zinc, tin, such as for example dibutyltin dilaurate (DBTL), titanium tetraisopropylate or bismuth/zinc carboxylates.

The appropriate quantity of diisocyanate (B1) or (B2) is introduced into the appropriate quantity of polyether polyol (A1) or (A2) which is previously fed into the reactor of step a1) or a2), said step being preferably performed at a temperature from 50° C. to 100° C.

Step b1) in the Process for Manufacturing (P1)

According to step b1), the polyurethane (C1) obtained from step a1) reacts with an alpha, beta or gamma aminosilane (D1) of formula (V):

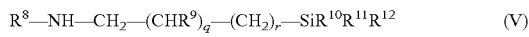

$$R^8-NH-CH_2-(CHR^9)_q-(CH_2)_r-SiR^{10}R^{11}R^{12} \quad (V)$$

wherein:
- $R^8$ and $R^9$, identical or different, represent a hydrogen atom or a C1-C10 aliphatic or aromatic hydrocarbon radical which can be linear, branched or cyclic;
- $R^{10}$ represents a C1-C10 alkyl radical, linear or branched or has the same definition as $R^{11}$ or $R^{12}$;
- $R^{11}$ and $R^{12}$, identical or different, represent a C1-C8 linear or branched alkoxy radical or a C1-C8 acyloxy radical;
- q and r, identical or different, are equal to 0 or 1.

Preferably, an aminosilane (D1) of alpha type (corresponding to q=r=0) or of gamma type (corresponding to q=r=1) is used, because of its commercial availability.

Preferably, an aminosilane (D1) of formula (V) is used, wherein:
- $R^8$ represents a hydrogen atom or a C1-C6 alkyl radical or a C3-C6 cycloalkyl;
- $R^9$ represents a hydrogen atom;
- $R^{10}$ represents a group chosen from: methyl, ethyl, methoxy, ethoxy; and
- $R^{11}$ and $R^{12}$ represent a methoxy or an ethoxy group.

By way of example, mention may be made of:
alpha-aminosilane having the formula (VII):

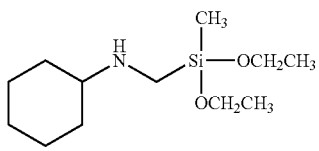

having a molar mass of 245.5 g, available from Wacker Chemie AG Company under the trader name Geniosil® XL 924;

alpha-aminosilane having the formula (VIII):

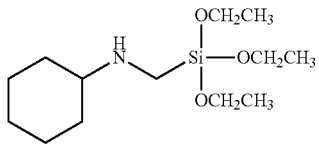

having a molar mass of 275.5 g, available from Wacker Chemie AG Company under the trade name Geniosil® XL 926;

gamma-aminosilane having the formula: nBu—NH—$(CH_2)_3$—$Si(OMe)_3$, having a molar mass of 235 g, available from Evonik Degussa Company under the trade name Dynasylan® 1189;

gamma-aminosilane having the formula: $NH_2$—$(CH_2)_3$—$Si(OMe)_3$ having a molar mass of 179.3 g, available from Momentive Company under the trade name Silquest® A-1110;

gamma-aminosilane having the formula: $NH_2$—$(CH_2)_3$—$Si(OEt)_3$ having a molar mass of 221.1 g, available from Momentive Company under the trade name Silquest® A1100.

According to a preferred embodiment, the aminosilane (D1) is a gamma-aminosilane (corresponding to q=r=1 in formula (V)).

Preferably, a gamma-aminosilane of formula (V) wherein $R^{10}$, $R^{11}$ and $R^{12}$ each represent an ethoxy group is used for the improved stability to moisture of the corresponding silyl-containing polyurethane (P1).

Advantageously, the quantity of aminosilane (D1) which reacts with the polyurethane (C1) obtained from step a1) corresponds to an equivalent ratio of mole number —NCO/mole number of (D1) ranging from 0.95 to 1.

Practically, the corresponding quantity of aminosilane (D1) introduced into the reactor is calculated from the mole number of —NCO groups comprised in the polyurethane (C1) obtained from step a1). This number, which is calculated and/or determined by analysis of the polyurethane (C1), comprises terminal —NCO groups of the polyurethane (C1) and the —NCO groups of isocyanate monomer (B1) which have not reacted at step a1). The excess of aminosilane (D1) ensures the reaction of all the NCO functions present in the products present during step a1), including the functions of isocyanate monomers (B1) having not reacted during the polycondensation reaction of step a1).

Preferably, step b1) is performed at a temperature ranging from 40 to 100° C.

At the end of step b1), the silyl-terminated polyurethane (P1) is obtained.

Step b2) in the Process for Manufacturing (P2)

The polyurethane-polyether block (C2) having —NCO terminal groups obtained at the end of step a2) reacts with a polyester polyol (D2), according to step b2) of the process.

The polyester polyols (D2) are chosen from aliphatic or aromatic polyester polyols, and mixtures thereof. Preferably, their average molecular mass is ranged from 1 to 10 kDa, more preferably from 2 to 6 kDa, and their hydroxyl functionality can vary from 2 to 4.

By way of example, mention may be made of:
polyester polyols of natural origin such as castor oil;
polyester polyols resulting from condensation:
- of one or more aliphatic (linear, branched or cyclic) or aromatic polyols such as ethanediol, 1,2-propanediol, 1,3-propanediol, glycerol, trimethylolpropane, 1,6-hexanediol, 1,2,6-hexanetriol, butenediol, sucrose, glucose, sorbitol, pentaerythritol, mannitol, triethanolamine, N-methyldiethanolamine and mixtures thereof, with
- one or more polycarboxylic acid or its ester or anhydride derivative such as 1,6-hexanedioic acid, dodecanedioic acid, azelaic acid, sebacic acid, adipic acid, 1,18-octadecanedioic acid, phthalic acid, succinic acid, and mixtures of those acids, a unsaturated anhydride such as maleic or phthalic anhydride, or a lactone such as caprolactone.

Many of those products are commercially available.

Among the polyester polyol (D2) that can be used in the process for manufacturing (P2), mention may be made of the following products having a hydroxyl functionality equal to 2:

KURARAY® Polyol P-1010, available from Kuraray Company, which derives from condensation of adipic acid and 6-methyl-1,5-pentyl diol having a molecular weight of 1000 Da, a hydroxyl number of 112, and being liquid at room temperature, TONE® 0240 (available from Union Carbide) which is a polycaprolactone having a molecular weight of about 2000 Da, an $I_{OH}$ equal to 56, and a melting point of about 50° C., DYNACOLL® 7381 having a molecular weight of about 3500 Da, an $I_{OH}$ equal to 30, and a melting point of about 65° C., DYNACOLL® 7360 which derives from condensation of adipic acid with hexanediol, a molecular weight of about 3500 Da, an $I_{OH}$ equal to 30, and a melting point of about 55° C., DYNACOLL® 7330 having a molecular weight of about 3500 Da, an $I_{OH}$ equal to 30, and a melting point of about 85° C., DYNACOLL® 7363 which derives from condensation of adipic acid with hexanediol, having a molecular weight of about 5500 Da, an $I_{OH}$ equal to 21 and a melting point of about 57° C., DYNACOLL® products are available from EVONIK Company.

Preferably, the polyester polyol (D2) used is a polycaprolactone, castor oil or a polyester polyol resulting from the condensation of ethanediol, 1,3-propanediol and/or 1,6-hexanediol with the adipic acid and/or phthalic acid.

Preferably, the polyester polyol used in step b2) has a —OH functionality ranging from 2 to 3, a functionality of 2 being particularly preferred.

During step b2), the polyurethane (C2) reacts with an excess of polyester polyol (D2) in term of equivalent functional groups. Preferably, the reactant quantities correspond to an —NCO/—OH equivalent ratio ranging from 0.10 to 0.80, said equivalent ratio being defined as previously. The quantities by weight of reactants to be fed into the reactor are determined on the basis of this ratio, as well as, regarding polyester polyol, on their hydroxyl index $I_{OH}$ whose definition is identical, mutatis mutandis, to the definition previously given for the polyether polyols.

Preferably, the polyester polyol used in step b2) has a melting point superior or equal to 55° C., corresponding to a significant crystallinity. In such a way, the "green strength" of the polyurethane obtained in the end is improved.

Preferably, for step b2), the appropriate quantity of polyester polyol (D2) is introduced into the appropriate quantity of polyurethane (C2) previously fed into the reactor. The reaction is preferably carried out at a temperature from 70 to 110° C.

Step c2) in the Process for Manufacturing (P2)

According to step c2), the polyurethane (E2) having —OH terminal groups obtained in the end of step b2) reacts with an isocyanatosilane (F2) of formula (VI):

$$NCO-R^3-Si(R^4)_p(OR^5)_{3-p} \quad (VI)$$

wherein:
R³ represents a linear alkylene divalent radical comprising from 1 to 3 carbon atoms;
R⁴ and R⁵, which are identical or different, each represent a linear or branched alkyl radical having 1 to 4 carbon atoms, with the possibility, when there are several R⁴ (or R⁵) radicals, that these radicals are identical or different;
p is an integer equal to 0, 1 or 2.

The isocyanatosilane of formula (VI) are commercially available. Mention may be made for example of the gamma-isocyanato-n-propyl-trimethoxysilane available under the trade name Geniosil® GF 40 or the alpha-isocyanato-methyl-dimethoxymethylsilane available under the trade name Geniosil® XL-42, both available from Wacker Company.

Preferably, the quantities of isocyanatosilane (F2) and of polyurethane having —OH terminal groups (E2) implemented during step c2) correspond to an equivalent ratio —NCO/—OH ranged from 0.95 to 1.05. Preferably, step c2) is conducted at a temperature of about 100° C.

At the end of step c2), the silyl-containing polyurethane (P2) is obtained.

Tackifying Resin

As regards the tackifying resin(s) which are included in the adhesive composition, the expression "compatible tackifying resin" means a tackifying resin which, when it is mixed in 50%/50% by weight proportions with the silyl-containing polymer gives a substantially homogeneous blend.

According to one embodiment of the invention, the tackifying resin is chosen from:
(i) phenol modified terpene resins,
(ii) hydrocarbon resins,
(iii) rosin ester resins, and
(iv) acrylic resins.

According to one embodiment, phenol modified terpene resins have a softening point from 110° C. to 130° C.

According to one embodiment, the hydrocarbon resins have a softening point from 70 to 120° C.

According to one embodiment, the rosin ester resins have a softening point from 90 to 110° C.

The softening point of the silyl-containing polymer and/or of the tackifying resin can be measured according to ASTM E28 standard.

According to one embodiment, phenol modified terpene resins are obtained by polymerization of terpene hydrocarbons and phenols, in the presence of Friedel-Crafts catalysts.

According to one embodiment, hydrocarbon resins are selected from:
resins obtained by a process comprising the polymerization of [alpha]-methyl-styrene, said process possibly also including a reaction with phenols,
resins obtained by hydrogenation, polymerization or copolymerization (with an aromatic hydrocarbon) of mixtures of unsaturated aliphatic hydrocarbons having around 5, 9 or 10 carbon atoms derived from petroleum fractions, optionally grafted with maleic anhydride,
terpene resins, generally resulting from the polymerization of terpene hydrocarbons such as, for example, monoterpene (or pinene) in the presence of Friedel-Crafts catalysts,
copolymers based on natural terpenes, for example styrene/terpene, [alpha]-methylstyrene/terpene and vinyl-toluene/terpene.

According to one embodiment, rosin ester resins are selected from natural or modified rosins, such as for example the rosin extracted from pine gum, wood rosin extracted from tree roots and their derivatives that are hydrogenated, dimerized, polymerized or esterified by monoalcohols or polyols such as glycerol.

According to one embodiment, the molecular weight of a non acrylic resin i), ii) or iii) as above-disclosed is inferior or equal to 10,000 Da, preferably inferior or equal to 2,000 Da, more preferably inferior or equal to 1,000 Da.

An acrylic resin is defined as a polymer or oligomer built with a significant amount of (meth)acrylic and/or (meth) acrylate monomers, preferably at least 5% weight/weight (w/w), more preferably at least 10% w/w, still more preferably at least 20% w/w, still more preferably at least 30% w/w in the polymeric chain.

According to one embodiment (meth)acrylic monomers are chosen from acrylic acid, methacrylic acid, methyl acrylate, methyl methacrylate, ethyl acrylate, ethyl methacrylate, butyl acrylate, butyl methacrylate, isobutyl acrylate, isobutyl methacrylate, n-hexyl acrylate, n-hexyl methacrylate, 2-ethylhexyl acrylate, ethylhexyl methacrylate, n-heptyl acrylate, n-heptyl methacrylate, stearyl acrylate, stearylmethacrylate, glycidyl methacrylate, alkyl crotonates, vinyl acetate, di-n-butyl maleate, di-octylmaleate, acetoacetoxyethyl methacrylate, acetoacetoxyethyl acrylate, acetoacetoxypropyl methacrylate, acetoacetoxypropyl acrylate, diacetone acrylamide, acrylamide, methacrylamide, hydroxyethyl methacrylate, hydroxyethyl acrylate, allyl methacrylate, tetrahydrofurfuryl methacrylate, tetrahydrofurfuryl acrylate, cyclohexylmethacrylate, cyclohexyl acrylate, n-hexyl acrylate, n-hexyl methacrylate, 2-ethoxyethyl acrylate, 2-ethoxyethyl methacrylate, isodecyl methacrylate, isodecyl acrylate, 2-methoxy acrylate, 2-methoxy methacrylate, 2-(2-ethoxyethoxy) ethylacrylate, 2-phenoxyethyl acrylate, 2-phenoxyethyl methacrylate, isobornyl acrylate, isobornyl methacrylate, caprolactone acrylate, caprolactone methacrylate, polypropyleneglycol monoacrylate, polypropyleneglycol monomethacrylate, poyethyleneglycol(400) acrylate, polypropyleneglycol(400) methacrylate, benzyl acrylate, benzylmethacrylate, N-vinyl pyrrolidone or N-vinyl lactam.

Preferably, (meth)acrylic monomers have up to 20 carbon atoms, more preferably, (meth)acrylic monomers are chosen from acrylic acid, methacrylic acid, butyl acrylate, 2-ethylhexyl acrylate and hydroxyethylacrylate.

According to one embodiment, acrylic resins are selected from polymers containing at least one (meth)acrylic function or chain part and at least one hydrocarbon chain part, said polymers can be in the form of copolymers, grafted or reacted or block polymers.

Those resins have a viscosity measured at 100° C. significantly superior or equal to 100 Pa·s, and inferior or equal to 100 Pa·s at 150° C. Resins of type (iv) can comprise repeating units of at least one hydrocarbon monomer and at least one acrylate monomer. Hydrocarbon monomers are selected from the group consisting of styrene, alpha-methyl styrene, vinyl toluene, indene, methylindene, divinylbenzene, dicyclopentadiene, and methyl-dicyclopentadiene, and polymerizable monomers contained in C5-pyperylenic and C5-isoprene and C9-aromatic available streams from the petrochemical industry. Those hydrocarbon monomers are usually polymerized together in various ratios by cationic polymerization using lewis acid catalysts. Acrylate monomers have the general formula Ra—CH=CRb—COORc wherein Ra, Rb, Rc are selected independently from each other from the group consisting of hydrogen, aliphatic groups, and aromatic groups. Acrylate monomers are selected from the group consisting of methyl acrylate, acrylic acid, methacrylic acid, methylmethacrylate, ethyl acrylate, ethylmethacrylate, butyl acrylate, butylmethacrylate, isobutyl acrylate, isobutylmethacrylate, n-hexyl acrylate, n-hexylmethacrylate, ethylhexyl acrylate, ethylhexyl methacrylate, n-heptyl acrylate, n-heptyl methacrylate, 2-methyl heptyl(meth)acrylate, octyl acrylate, octyl methacrylate, isooctyl(meth)acrylate, n-nonyl(meth)acrylate, isononyl(meth)acrylate, decyl(meth)acrylate, isodecyl acrylate, isodecyl methacrylate, dodecyl(meth)acrylate, isobornyl (meth)acrylate, lauryl methacrylate, lauryl acrylate, tridecyl acrylate, tridecyl methacrylate, stearyl acrylate, stearylmethacrylate, glycidylmethacrylate, alkyl crotonates, vinyl acetate, di-n-butylmaleate, di-octylmaleate, acetoacetoxyethyl methacrylate, acetoacetoxyethyl acrylate, acetoacetoxypropyl methacrylate, acetoacetoxypropyl acrylate, diacetone acrylamide, acrylamide, methacrylamide, hydroxyethylmethacrylate, hydroxyethyl acrylate, allyl methacrylate, tetrahydrofurfuryl methacrylate, tetrahydrofurfuryl acrylate, cyclohexyl methacrylate, cyclohexyl acrylate, n-hexyl acrylate, n-hexyl methacrylate, 2-ethoxyethyl acrylate, 2-ethoxyethyl methacrylate, isodecyl methacrylate, isodecyl acrylate, 2-methoxy acrylate, 2-methoxy methacrylate, 2-(2-ethoxyethoxy)ethylacrylate, 2-phenoxyethyl acrylate, 2-phenoxyethyl methacrylate, isobornyl acrylate, isobornyl methacrylate, caprolactone acrylate, caprolactone methacrylate, polypropyleneglycol monoacrylate, polypropyleneglycol monomethacrylate, poyethyleneglycol(400) acrylate, polypropyleneglycol(400) methacrylate, benzyl acrylate, benzylmethacrylate, sodium 1-allyloxy-2-hydroylpropyl sulfonate, acrylonitrile, and mixtures thereof.

Preferably hydrocarbon monomers are selected among the group of aromatic monomers or polymerizable monomers from the C9-aromatic stream from petrochemical sources; of dicyclopentadiene or polymerizable monomers from the C5-pyperylene or C5-isoprene stream from petrochemical sources.

Preferably acrylate monomers are acrylic acid and 2-ethylhexyl acrylate, hydroxyethylacrylate, methacrylic acid, butyl acrylate. Softening point of such resins are preferably from room temperature up to 180° C., molecular weights range in weight average is preferably from 200 to 25000 Daltons, and acid number preferably ranging from 0 to 300 mg KOH/g. Preferred resins would have molecular weight inferior or equal to 10,000 Daltons, more preferably inferior or equal to 2,000 Da, most preferably inferior or equal to 1,000 Da; softening point inferior or equal to 150° C., more preferably inferior or equal to 120° C., most preferably ranging from 70 to 120° C.; acid number inferior or equal to 150 mg KOH/g, more preferably inferior or equal to 100 mg KOH/g, most preferably from 10 to 100 mg KOH/g.

According to one embodiment, the molecular weight of an acrylic resin is inferior or equal to 300,000 when only one resin is present in the adhesive composition, preferably inferior or equal to 100,000, most preferably inferior or equal to 20,000.

A non-acrylic resin can still contain some acrylic functions in a non-significant quantity, either being part of the polymerization chemical reaction, or as grafted or functionalized groups onto monomers or onto the polymeric chains.

Such resins are commercially available or described in literature; for example, mention may be made of the following products:

resins of type (i): DERTOPHENE® H150 available from DRT company with a molecular weight Mn equal to around 630 Da, DERTOPHENE® T having a molecular weight equal to around 500 Da available from the same company;

resins of type (ii): NORSOLENE® W110 available from Cray Valley, which is obtained by polymerization of alpha-methylstyrene without the action of phenols, with a number-average molecular weight of 1000 Da, and a softening point of 110° C., NORSOLENE® W80 is of the same structure as NORSOLENE® W110 but with a lower molecular weight leading to a softening point of 80° C.;

resins of type (iii): SYLVALITE® RE 100 which is a pentaerythritol rosin ester available from Arizona Chemical and having a molecular weight Mn of around 1700 Da, resins of type (iv):
- KOLON® PX95 (available from Kolon Industries Inc.) or Eastman® resin described in U.S. Pat. No. 7,332,540 (formulation 1, table 3 column 14), which are polymers containing at least one (meth)acrylic function or chain part and at least one hydrocarbon chain part, said polymers can be in the form of copolymers, grafted or reacted or block polymers,
- Acronal® 4F available from the BASF Company, Germany, resulting from polymerization of butyl acrylate monomers.

Catalyst

The curing catalyst that can be used in the composition according to the invention may be any catalyst known to a person skilled in the art for silanol condensation. Mention may be made, as examples of such catalysts, of organic derivatives of titanium such as titanium acetyl acetonate (commercially available under the name TYZOR® AA75 from DuPont), of aluminium such as aluminium chelate (commercially available under the name K-KAT® 5218 from King Industries), of amines such as 1,8-diazobicyclo[5.4.0]undec-7-ene or DBU.

Optionally, the adhesive composition according to the invention may also include, in combination with the silyl-containing polymer, thermoplastic polymers often used in the preparation of HMPSAs, such as ethylene vinyl acetate (EVA) or styrene block copolymers.

The curable adhesive composition according to the invention may also comprise up to 3% of a hydrolysable alkoxysilane derivative, as a desiccant, and preferably a trimethoxysilane derivative. Such an agent advantageously prolongs the shelf life of the composition according to the invention during storage and transport, before the use thereof. Mention may be made, for example, of [gamma]-methacryloxypropyltrimethoxysilane available under the trade name SILQUEST® A-174 from US Momentive Performance Materials Inc.

The adhesive composition according to the invention may also include a plasticizer such as a phthalate like diisononylphthalate (DINP) or a benzoate, a paraffinic and naphthenic oil (such as PRIMOL® 352 from Esso) or else a wax of a polyethylene homopolymer (such as A-C® 617 from Honeywell) or a wax of a polyethylene/vinyl acetate copolymer, or else pigments, dyes or fillers.

Finally, an amount of 0.1 to 3% of one or more stabilizers (or antioxidants) is preferably included in the composition according to the invention. These compounds are introduced to protect the composition from degradation resulting from a reaction with oxygen which is capable of being formed by action of heat or light. These compounds may include primary antioxidants which trap free radicals and are, in particular, substituted phenols such as IRGANOX® 1076 or IRGANOX® 1010 from Ciba. The primary antioxidants may be used alone or in combination with other secondary antioxidants or UV stabilizers.

The adhesive composition may be prepared by a process which comprises:
- a step of mixing in an air-free environment, preferably under an inert atmosphere, the silyl-containing polymer with the tackifying resin(s), at a temperature from 50 to 170° C., preferably from 100 to 170° C.; then
- a step of cooling said mixture to a temperature ranging from 50 to 90° C., and advantageously of around 70° C.; then
- a step of incorporating a catalyst into said mixture and, where appropriate, desiccant and other optional components.

As used herein, the term "self-adhesive article" is meant to include any article which can be bonded onto a surface only by the action of a pressure with the hand or with an equipment, without the use of additional adhesives. By "self-adhesive article" is also to be understood a Pressure Sensitive Adhesive. Those articles aim at exposing a PSA surface for use of sticking to other surfaces for closing, maintaining, fastening, or simply immobilizing, exposing forms, logos, pictures or information. Those articles can be used in many fields, such as medical, clothing, packaging, automobile or construction field. They can be shaped according to their final application, for example in the form of tapes, such as industrial tape, DIY tape, single or double side tape, double side tape made out of single or multiple or no carrier, tape made with specific carriers like open or closed cells foams, grids or composite or textile or extruded or laminated webs, or in the form of labels, bandages, wound dressing, blisters, electrode pads, plasters, patches, PSA coated thick pad, road marking tapes or labels, graphic art PSA films.

The substrate can be any material having a Moisture-Vapor Transmission Rate (MVTR) superior or equal to 1000 g/m$^2$/24 h, preferably superior or equal to 2000 g/m$^2$/24 h, more preferably superior or equal to 3000 g/m$^2$/24 h. Preferably, the MVTR of the substrate is superior or equal to the MVTR of the adhesive layer.

According to one embodiment, there is no substrate in addition to the adhesive material, used as itself as a double-sided PSA article.

According to one embodiment of the invention, the substrate is chosen from polyester, polyurethane, polyester block amide or porous polyethylene materials. The substrate can be of woven or non-woven materials.

Examples of such materials are prepared from:
- Estane™ 58309NAT022 polyurethane materials (B.F. Goodrich, Cleveland, Ohio),
- Rucothane™ polyurethane or HytreFM 4056 elastomeric polyester (DuPont, Wilmington, Del.),
- Pebax™ 2533 or 3533 polyether block amide (Arkema, Paris, France).

Preferably, the coating of the adhesive composition on the substrate is continuous or quasi-continuous.

As used herein, the "adhesive layer" is the cured adhesive composition.

Herein, by "curing" it is to be understood "cross-linking", at a molar ratio that is sufficient to provide requested functions in specific conditions of use.

According to one embodiment of the invention, the adhesive layer having a coating weight inferior to 50 g/m$^2$ has a MVTR superior or equal to 300 g/m$^2$/24 h, preferably superior or equal to 500 g/m$^2$/24 h, more preferably superior or equal to 1000 g/m$^2$/24 h, more particularly superior or equal to 2000 g/m$^2$/24 h.

According to one embodiment, the adhesive layer having a coating weight inferior or equal to 30 g/m$^2$, has a MVTR superior or equal to 500 g/m$^2$/24 h, preferably superior or equal to 750 g/m$^2$/24 h, more preferably superior or equal to 1000 g/m$^2$/24 h.

According to one embodiment, the adhesive layer having a coating weight superior or equal to 50 g/m$^2$ has a MVTR superior or equal to 100 g/m$^2$/24 h, preferably superior or equal to 200 g/m$^2$/24 h, more preferably superior or equal to 400 g/m$^2$/24 h, more particularly superior or equal to 1000 g/m$^2$/24 h.

Another object of the invention is a self-adhesive article comprising at least one breathable substrate having a Moisture-Vapour Transmission Rate superior or equal to 1000 g/m²/24 h, wherein at least one face of said substrate is coated with an adhesive layer obtained by curing an adhesive composition as previously described.

Preferably, the adhesive layer is continuous or quasi-continuous.

Some of those compositions are described in documents WO 2009/106699 and EP 2336 208 but the adhesive layer obtained by curing those adhesive compositions are not associated with a breathable substrate.

According to one embodiment, the self-adhesive article has a breathable adhesive layer, said breathable adhesive layer being characterized by a MVTR superior or equal to 300 g/m²/24 h, preferably superior or equal to 500 g/m²/24 h, more preferably superior or equal to 1000 g/m²/24 h for a coating weight inferior to 50 g/m².

According to one embodiment, the self-adhesive article has a breathable adhesive layer, said breathable adhesive layer being characterized by a MVTR superior or equal to 500 g/m²/24 h, preferably superior or equal to 750 g/m²/24 h, more preferably superior or equal to 1000 g/m²/24 h, still more preferably superior or equal to 1500 g/m²/24 h for a coating weight inferior to 30 g/m².

According to one embodiment, the self-adhesive article has a breathable adhesive layer, said breathable adhesive layer being characterized by a MVTR superior or equal to 100 g/m²/24 h, preferably superior or equal to 200 g/m²/24 h, more preferably superior or equal to 400 g/m²/24 h for a coating weight superior or equal to 50 g/m².

The self-adhesive article of the invention satisfies the technical requirements for a Pressure-Sensitive Adhesive which are:
- a peel test result superior or equal to 0.39 N/cm, preferably with a clean peel,
- a shear resistance under 1 kg at room temperature superior or equal to 10 minutes, preferably superior or equal to 60 minutes, more preferably superior or equal to 1 day,
- a loop tack superior or equal to 0.79 N/cm, preferably with a clean peel, Preferably, those tests are initiated at least 24 h after curing the PSA coating.

Another object of the present invention is a process for manufacturing the self-adhesive article of the invention, comprising the steps of:
(a) conditioning the adhesive composition as previously defined at a temperature from 20 to 160° C.; then
(b) coating the adhesive composition obtained at step a) onto a carrying surface; then
(c) curing the coated adhesive composition, by heating the coated substrate at a temperature from 20 to 200° C. optionally,
(d) laminating the cured adhesive layer onto a substrate having a Moisture-Vapor Transmission Rate superior or equal to 1000 g/m²/24 h.

The step (b) of coating the substrate is carried out using known coating devices, such as for example a lipped die or a curtain-coating type die, or else a roll. It employs a weight per unit area of adhesive composition ranging from 3 to 2000 g/m², preferably from 5 to 500 g/m², more preferably from 10 to 250 g/m².

The carrying surface is adapted to carry the adhesive composition. The carrying surface can be a release liner or a carrier film or web.

According to one embodiment, the carrying surface is a siliconized surface.

Preferably, the coating is continuous or almost continuous.

According to one embodiment, the coated adhesive composition is further submitted to a treatment step in a humid atmosphere characterized by its humidity level. Preferably, the humidity atmosphere is an atmosphere in which from 5 to 100% of the molecules are water molecules, preferably from 10% to 90%, more preferably from 15% to 70% of the molecules are water molecules.

The time needed for the curing of step (c) may vary to a large extent, for example from 1 second to 10 minutes, depending on the weight per unit area of adhesive composition deposited on the substrate, on the heating temperature and on the humidity.

This curing step has the effect of creating between the polymer chains and under the action of atmospheric moisture, siloxane-type bonds which result in the formation of a three-dimensional polymer network. The thus cured adhesive composition is a pressure-sensitive adhesive layer which gives the substrate that is coated therewith desirable adhesive strength and tack.

Another object of the invention is an adhesive composition comprising:
- at least one silyl-containing polymer,
- at least one compatible tackifying resin selected from polymers containing at least one (meth)acrylic function or chain part and at least one hydrocarbon chain part,
- at least one catalyst.

The polymers containing at least one (meth)acrylic function or chain part and at least one hydrocarbon chain part can be in the form of copolymers, grafted or reacted or block polymers, The silyl-containing polymer of the adhesive composition can be the same as previously described.

The catalyst can be the same as previously described.

According to one embodiment, the tackifying resin is selected from:
- a mixture of styrene-acrylic resins and rosin ester resins, and
- a dicyclopentadiene-acrylic polymer, said polymer can be in the form of a copolymer, a grafted or reacted or block polymers.

According to one embodiment, the adhesive composition comprises:
- from 20 to 85%, preferably from 30 to 75% by weight of at least one silyl-containing polymer,
- from 15 to 80%, preferably from 25 to 70% by weight of at least one tackifying resin,
- from 0.01 to 3%, preferably from 0.1 to 2% by weight of at least one catalyst.

According to one embodiment, the adhesive composition is capable of being used according to the present invention.

According to one embodiment, the adhesive composition gives after curing an adhesive layer having a MVTR superior or equal to 500 g/m²/24 h, preferably superior or equal to 750 g/m²/24 h, more preferably superior or equal to 1000 g/m²/24 h, in particular for a coating weight inferior or equal to 30 g/m².

EXAMPLES

Description of the products used in the compositions of the examples:
Desmoseal® XP2636 is a Silane-terminated polyether material available from the Company Bayer, Germany, with a viscosity of 35,000 mPa·s at 23° C. (according to ASTM standard D1236), and a tensile strength of 0.77 MPa and elongation at break of 133% in tensile test performed according to standard ISO 37 at room temperature.

SPUR® 1050MM is a silane-terminated polyurethane available from the Company Momentive, Germany, with a viscosity of 35,000 mPa·s at 23° C. (according to ASTM standard D1236), and a tensile strength of 0.68 MPa and elongation at break of 150% in tensile test performed according to standard ISO 37 at room temperature.

XPS 18446 is produced as described in patent application US20110052912 as polymer A with a final viscosity of about 55,000 mPa·s (according to ASTM standard D1236), and a tensile strength of 0.83 MPa and elongation at break of 230% in tensile test performed according to standard ISO 37 at room temperature.

Poly15 (silyl-containing polymer of type P2) is produced according to the following process:

Step (a2): synthesis of a polyurethane with 2-NCO end groups and one or more polyether blocks:

In a closed reactor of 250 ml, equipped with a stirrer, heating means, thermometer and connected to a vacuum pump was charged 96.89 g of polyether polyol Acclaim® 12200, having a molecular weight in number of 12000 Da, a hydroxyl number of 10 mg KOH/g (corresponding to an equivalent number of —OH functions equal to 0.178 mmol/g). The material is heated to 80° C. and maintained at a reduced pressure of 20 mbar for 1 hour in order to dehydrate the polyether polyol.

Then, 0.1 g of a bismuth carboxylate/zinc catalyst (Borchi Kat® VP0244 available from Borchers GmbH Company) diluted in methyl ethyl ketone solvent at 90% in weight, and 3.01 g of isophorone diisocyanate (containing 37.6% by weight of NCO functions), are introduced into the reactor. The mixture is maintained at atmospheric pressure and heated to 90° C. The quantities introduced thus corresponding to a ratio NCO/OH equal to 1.56. The polyaddition reaction is allowed to last for 3 hours to obtain 100 g of a polyurethane having a NCO function content (followed by potentiometric titration) equal to 9.71 mmol/g, corresponding to the consumption of all hydroxyl functions originating from initial polyether polyol quantity Step (b2): synthesis of a polyurethane block polyether and polyester terminated with —OH terminal groups:

11.52 g of Kuraray® P1010 polyester polyol (having a hydroxyl number of 112 mg KOH/g corresponding to an equivalent OH number function equal to 1.99 mmol/g) is charged in a closed reactor of 250 ml equipped with a stirrer, heating means, thermometer and connected to a vacuum pump. The material is heated to 80° C. and maintained at a reduced pressure of 20 mbar for 1 hour to dehydrate the polyester polyol.

85.38 g of polyester diol and polyurethane prepolymer obtained in step (a2) is then introduced, thus corresponding to a NCO/OH ratio of 0.6.

The reactor is then maintained under reduced pressure of 20 mbar and heated to 100° C., and polyaddition reaction is progressing for 3 hours until complete consumption of the —NCO polyurethane of step (a2), detected by the progressive disappearing of the NCO peak area by infra-red spectroscopy analysis.

This results in 96.9 g of polyurethane with a —OH functions content of 14.74 mmol/g.

Step (c2): synthesis of a polyurethane block polyether and polyester with alkoxy silyl terminal groups:

3.1 g of gamma-isocyanato-n-propyl-trimethoxysilane (containing 19.9% by weight of NCO functions) is then introduced into the reactor after step (b2) is completed, leading to a mixture where ratio of NCO/OH functions is equal to 1.

The reactor was then kept under inert atmosphere at 100° C. for 90 minutes until complete reaction occurred, detected by the disappearing of the NCO peak area by infra-red analysis.

100 grams of a polyurethane block polyether and polyester with alkoxy silyl end groups are obtained. Viscosity of this resulting material is measured by a Brookfield RTV viscosimeter at 23° C. and at a speed of 20 rpm with a spindle 6, at 70 000 mPa·s Poly5 (corresponding to silyl-containing polymer of type P1)

This polymer is prepared according to the process previously described for the polymer P1.

Step (a1): preparation of a polyurethane (C1) having —NCO terminal groups.

Use is made of:

as polyether polyol (A1): difunctional polypropylene glycol (PPG) having a molecular weight of 4000 Da and a hydroxyl index equal to 28 mg KOH/g;

as diisocyanate (B1): Isophorone diisocyanate (IPDI) containing 37.6% w/w of —NCO groups (corresponding to an equivalent number of —NCO functions equal to 8.95 mmol/g).

In a closed reactor of 250 mL, equipped with a stirrer, heating means, a thermometer and connected to a vacuum pump, 84.89 g of polyether polyol (A1) are introduced. The reactor is then heated to 80° C. and maintained under reduced pressure of 20 mbar for 1 hour in order to dehydrate the polyether polyol.

We introduce in the reactor maintained at atmospheric pressure and heated to 90° C.:

4.2 mg of a bismuth/zinc carboxylate catalyst (Borchi® Kat VP0244 from Borchers GmbH Company), and 8.70 g of IPDI (containing 37.6% w/w of —NCO group), the quantities introduced correspond to a NCO/OH ratio equal to 1.8.

The polyaddition reaction is continued for 4 hours, until entire consumption of the hydroxyl functions of the polyether polyol.

The NCO-content (expressed in % weight/weight) of the product (C1) is followed by a potentiometric titration with an amine, until the aimed value of 1.6% w/w is obtained.

Step (b1): preparation of the silyl-containing polyurethane "poly5"

We introduce in the reactor in the end of step (a1), 6.40 g of gamma-aminosilane (D1) Silquest® A1110, corresponding to a ratio NCO/NR$^8$ equal to 1.

The reactor is then maintained under inert atmosphere at 100° C. for 1.5 hours, until complete reaction is achieved (detected by the disappearance of the NCO-band at infrared analysis).

We obtain 100 g of silyl-containing polymer "poly5" having a viscosity at 23° C. measured by a viscosimeter Brookfield RTV equal to 96 Pa·s.

Poly3 (corresponding to a silyl-containing polymer of type P1)

Step (a1) preparation of a polyurethane (A)-NCO end groups:

Use is made of:
as polyether polyol (A2): Voranol® EP1900 having a hydroxyl index equal to 28 mg KOH/g (corresponding to an equivalent number of —OH function equal to 0.50 mmol/g), and
as diisocyanate (B2): an IPDI containing 37.6% w/w of —NCO group (corresponding to an equivalent number of —NCO functions equal to 8.95 mmol/g).

In a closed reactor of 250 ml, equipped with a stirrer, heating means, thermometer and connected to a vacuum pump was charged 81.85 g of polyether polyol (A2) (ie: 40.85 mmol of —OH functions). The mixture is heated to 80° C. and maintained at a reduced pressure of 20 mbar for 1 hour to dehydrate the polyether polyol.

Then, we introduce into the reactor maintained at atmospheric pressure and heated to 90° C.:
0.1 g of a catalyst bismuth/zinc carboxylate (Borchi Kat® VP0244 Borchers GmbH Comapny) diluted with 90 wt % of MEK and
8.19 g of IPDI (ie: 73.32 mmol in NCO-functions) the quantities introduced thus corresponding to a ratio NCO/OH equal to 1.8.

The polyaddition reaction was continued for 4 hours until complete consumption of the hydroxyl groups of the polyether polyol, in order thus to obtain 90.14 g of a polyurethane having —NCO terminal groups (C2), which corresponds to about 32.5 mmol of NCO-functions.

The content of NCO-functions (expressed in % w/w) of the product formed during the reaction is followed by potentiometric titration with an amine, until the target value corresponding to 1.52% is reached.

We then introduce into the reactor, 5.85 g of Unilin® 425 (a linear polymeric mono-alcohol of structure C14-C54, of $I_{OH}$=98 mg KOH/g and of melting point=91° C., available from Baker Petrolite), thus corresponding to a NCO/OH ratio equal to 1.44.

The reactor was then kept under inert atmosphere at 100° C. for 1.5 hours until complete reaction is achieved (detected by the disappearance of the NCO-band in the infrared analysis).

This gives 95.98 g of a polyurethane (E2) having —NCO terminal group, which represents approximately 22.28 mmol of NCO-functions.

Step (b1) preparation of silyl-containing polyurethane "poly3" (type P1):
We then introduce into the reactor at the end of step a1), 4 g of aminosilane SILQUEST® A1110 (molecular mass=179 g/mol), thus corresponding to a final NCO/OH ratio equal to 1.
The reactor was then kept under inert atmosphere at 100° C. for 1.5 hours until complete reaction is achieved (detected by the disappearance of the NCO-band in the infrared analysis).
We obtain 100 grams of a silyl-containing polyurethane "poly3". Its viscosity at 50° C. measured by a Brookfield RTV was 57 Pa·s.

Acronal DS3500 is a tackifying resin (type iv) available from the Company BASF, Germany, comprising methyl acrylate monomers at 91% by weight, and acrylic acid at 9% by weight analyzed by proton and carbon NMR.

Acronal® 4F is a tackifying resin (type iv) available from the Company BASF, Germany, resulting from polymerization of n-butyl acrylate monomers.

Kolon PX95 is a product from copolymerization of C5-type monomers (68% in weight) with acrylic monomers (acrylic acid 4% in weight, butyl acrylate at 28% in weight analyzed by proton and carbon NMR), available from the Company Kolon Industries, Inc., Korea. It has a softening point of 100° C., an acid number of 20 mgKOH/g according to analysis test standard ASTM D974, and a molecular weight of 720 averaged in number analyzed by gel permeation chromatography. Its viscosity at 100° C. is significantly higher than 100 Pa·s.

Eastman resin described in U.S. Pat. No. 7,332,540 (formulation 1, table 3 column 14) is a tackifying resin (type iv) produced as described in patent document U.S. Pat. No. 7,332,540. Its features are exhibited in table 3 columns 14 and 15 as being composed by Styrene monomer at 61% in weight, 2-ethylehexylacrylate at 31% in weight, and acrylic acid at 9% in weight. It also contains less than 2% in weight of diterbutylperoxide. Its softening point is 100° C., and its acid number is 60 mg KOH/g. Its molecular weight in z-average is 15,000 daltons. Its viscosity at 100° C. is significantly higher than 100 Pa·s.

2-ethylhexyl acrylate monomers, acrylic acid monomers, and melamine formaldehyde are available from Aldrich France.

1) Preparation of the Adhesive Compositions 1-1) Example A (Reference Composition Described in Table 1)

Example A is a solvent-based acrylic polymer prepared using the ingredients listed in table 1.

A polymerization reactor equipped with a heating jacket, nitrogen inlet valve, stirring mechanism, and reflux condenser was purged with nitrogen, the heating jacket was set to 80° C., and the initial solvent (ethyl acetate) charge was added, for about 70% of the total solvent quantity. The stirring mechanism was set to 125 round per minute. A monomer mixture was added in a small amount (around 15% of the whole monomer quantity) as the initial monomer charge, and mixed for ten minutes, and the content of the reactor was heated to reflux. After kick-off (70° C.) the batch was held for 15 minutes, with agitation. The monomer introduction was set at about 3 g/minutes, and the batch temperature was maintained at 70-80° C. After the whole monomer feed was added, the reactor content was held for one hour, with agitation. The catalyst (melamine formaldehyde) was then added. Final charge of solvent was added to reach a calculated level of 35% polymer content into solvent, and the reactor contents were cooled and discharged.

1-2) Example 1 to 14 (Composition Described in Table 1 and Table 1bis)

The compositions that appear in the tables 1 and 1bis below are prepared by firstly introducing the tackifying resin into a glass reactor under vacuum and heating to around 160° C. Then, once the resin is thoroughly molten, the silane-containing polymer is added.

The mixture is stirred under vacuum for 15 minutes, then cooled to 70° C. The catalyst (K-KAT® 5218) is then introduced. The mixture is kept under vacuum and continues to be stirred for another 10 minutes.

The mixture at lab scale is placed in a cartridge closed with two cups and anti-moisture agents to avoid uncontrolled curing.

TABLE 1 compositions

| (weight %) | A | 1 | 2 | 3 | 4 | 5 | 6 | 7 |
|---|---|---|---|---|---|---|---|---|
| Dertophene ® H150 |  | 48 |  |  |  |  |  |  |
| Norsolene ® W110 |  |  |  |  | 48 |  |  |  |
| Norsolene ® W80 |  |  | 48 |  |  |  |  |  |
| Sylvalite ® RE100 |  |  |  | 24 |  |  |  | 48 |
| Eastman ® resin |  |  |  |  |  |  |  |  |
| Kolon ® PX95 |  |  |  |  |  |  | 48 | 33 |
| Acronal ® 4F |  |  |  |  | 24 |  |  |  |
| Ac Resin ® DS3500 |  |  |  |  |  |  | 15 |  |
| XPS ®18446 |  | 50 | 50 | 50 | 50 | 50 | 50 | 50 |
| 2-ethylhexyl acrylate monomer | 31.5 |  |  |  |  |  |  |  |
| acrylic acid | 2.1 |  |  |  |  |  |  |  |
| melamine formaldehyde | 1.4 |  |  |  |  |  |  |  |
| ethyl acetate | 65 |  |  |  |  |  |  |  |
| catalyst |  | 2 | 2 | 2 | 2 | 2 | 2 | 2 |

TABLE 1bis

Compositions

| (weight %) | 8 | 9 | 10 | 11 | 12 | 13 | 14 |
|---|---|---|---|---|---|---|---|
| Dertophene ® H150 | 48 | 48 |  |  |  |  |  |
| Sylvalite ® RE100 |  |  |  |  |  |  | 24 |
| Eastman ® resin |  |  |  |  |  |  | 24 |
| Kolon ® PX95 |  |  | 33 | 33 | 33 | 33 |  |
| Ac Resin ® DS3500 |  |  | 15 | 15 | 15 | 15 |  |
| SPUR ® 1050MM |  |  | 50 | 50 |  |  |  |
| Desmoseal ® XP2636 |  | 50 |  |  |  |  |  |
| "Poly15" |  |  |  |  | 50 |  |  |
| "Poly5" |  |  |  |  |  | 50 |  |
| "Poly3" |  |  |  |  |  | 50 | 50 |
| catalyst | 2 | 2 | 2 | 2 | 2 | 2 | 2 |

2) Preparation of the tested laminates on PET substrate for technical performance evaluations and on non woven substrate (NW) for breathability evaluation, said NW substrate commercially available from Dounor company, France, being made with spunbond process of polypropylene fibers at a coating weight of 15 g/m², and having a MVTR equal to 7000 g/24 h/m², said substrates being coated with the adhesive composition according to paragraph 1), with a coating weight of 20 g/m², 35 g/m² or 50 g/m² at laboratory scale.

2-1) Laminates with Example A:

Following polymerization, the wet adhesive was coated on a siliconized release liner with the help of a Meier bar and a hand coater with controlled speed to get the target coating weight. Once the coating is done, it is stored in a ventilated area for 10 minutes at room temperature, and then dried at 120° C. for 5 minutes in a ventilated oven adapted to solvent based product. Then, the coated layer is laminated onto the non woven NW or PET 50 µm carrier. All laminates were stored for minimum 1 week before testing in a climate room at 23° C. and 50% relative humidity.

2-2) Laminates with Examples 1 to 14:

The adhesive composition obtained in 1) is preheated to a temperature between 80° C. and 100° C. in a cartridge heater. Then the adhesive is extruded through a slot die at the desired coating weight with the help of a pump. The slot die applied the adhesive onto a siliconized film (or onto a release paper) at a controlled coating weight of 20 g/m² or 30 g/m² or 50 g/m².

The coating is placed in a ventilated oven containing a small amount of moisture at 120° C. for 8 minutes for the curing process. After the curing, the coating is then laminated onto the Non Woven substrate or the 50 µm PET substrate. Laminated pressure applied is around 3 bars.

Breathability Test:

Use is made of the non woven laminates produced according to the process described in paragraph 2). Reference is made, for this test, to the NF EN 13726-2 standard. The principle is the following:

- the test is done at least 24 h after the curing step. The laminates are stored during 24 h in a controlled room at 23° C. and 50% of relative humidity before the test;
- 5 Moisture-Vapor Transmission Rate cups are filled with 20 mL of deionised water, 5 cups per test;
- 5 discs of 50 mm diameter per test are cut or die cut properly into the laminate. The release paper is then delaminated and the coating of the surface is visually inspected to confirm that 100% of the non woven substrate is covered by the adhesive;
- each disc is bonded onto the top of their dedicated MVTR cup;
- the cup is closed and we make sure that the closure is water proof as described in the standard, with a silicon gasket and seal;
- each cup is weighed and placed in an incubator oven at 37° C. with a humidity content below 20%. Weight is recorded as: $W_{initial}$. The cups are stored during 24 h in this incubator;
- when this time is over, each cup is weighted again and weight is recorded as: $W_{final}$. Then, the MVTR is calculated with the following calculation: MVTR= $(W_{initial} - W_{final}) \times 1000$.

The results are indicated in table 2.

TABLE 2 breathability results

| | MVTR (g/m²/24 h) | | |
|---|---|---|---|
| | 20 g/m² | 35 g/m² | 50 g/m² |
| A | 820 |  |  |
| 1 | 884 | 440 | 245 |
| 2 | 2374 |  |  |
| 3 | 2675 | 1573 |  |
| 4 | 1565 | 1128 |  |
| 5 | 1655 | 1169 |  |
| 6 | 1968 | 1617 |  |
| 7 | 2296 |  |  |
| 8 |  | 631 | 350 |
| 9 | 681 | 498 | 310 |
| 10 | 1992 | 1678 | 678 |
| 11 | 3412 |  |  |
| 12 | 2296 |  |  |
| 13 | 2065 |  |  |
| 14 | 1254 |  |  |

180° Peel Test on a Stainless Steel Plate 20 Minutes:

The adhesive strength is evaluated by the 180° peel test on a stainless steel plate as described in FINAT method No. 1 published in the FINAT Technical Manual, 6$^{th}$ edition, 2001.

FINAT is the international federation for self-adhesive label manufacturers and converters. The principle of this test is the following.

A test specimen in the form of a rectangular strip (25 mm×175 mm) is cut from the PET carrier coated with the cured composition obtained previously. This test specimen is, after the preparation thereof, stored for 24 hours at a temperature of 23° C. and in a 50% humidity atmosphere. It is then fastened over two-thirds of its length to a substrate constituted of a stainless steel plate. The assembly obtained is left for 20 minutes at room temperature. It is then placed in a tensile testing machine capable, starting from the end of the rectangular strip that is left free, of peeling or debonding the strip at an angle of 180° and with a separation rate of 300 mm per minute. The machine measures the force required to debond the strip under these conditions.

The corresponding results for a coating weight of 20 g/m² are expressed in N/cm and are indicated in table 3.

Tack Test (Also Known as Loop Test or Loop Tack Test):

The tack is evaluated by the loop tack test described in FINAT method No. 9, the principle of which is the following.

A test specimen in the form of a rectangular strip (25 mm×175 mm) is cut from the PET carrier coated with the cured composition obtained previously. This test specimen is, after the preparation thereof, stored for 24 hours at a temperature of 23° C. and in a 50% humidity atmosphere. The 2 ends of this strip are joined so as to form a loop, the adhesive layer of which is facing outward. The 2 joined ends are placed in the movable jaw of a tensile testing machine capable of imposing a rate of displacement of 300 mm/minute along a vertical axis with the possibility of moving back and forth. The lower part of the loop placed in the vertical position is firstly put into contact with a horizontal glass plate measuring 25 mm by 30 mm over a square area measuring around 25 mm per side. Once this contact has occurred, the displacement direction of the jaw is reversed. The tack is the maximum value of the force needed for the loop to be completely debonded from the plate.

The corresponding results for a coating weight of 20 g/m² are expressed in N/cm and are indicated in table 3. The failure profile is also indicated in table 3.

Resistance Time of the Adhesive Joint to Static Shear at 23° C.:

The stability of the adhesive strength of the PET carrier coated with the cured composition is evaluated, no later than one hour after it is obtained, by a test which determines the resistance time of the adhesive joint to static shear at 23° C.

Reference is made, for this test, to the FINAT method No. 8. The principle is the following.

A test specimen in the form of a rectangular strip (25 mm×75 mm) is cut from the PET support layer coated with the cured composition prepared previously. A square portion of 25 mm per side located at the end of the adhesive strip is fastened to a glass plate. The test plate thus obtained is maintained in a vertical position and the strip left free is connected to a weight of 1 kg. Under the effect of this weight, the adhesive joint which ensures the fastening of the strip to the plate is subjected to a shear stress. To better control this stress, the test plate is in fact placed so as to make an angle of 2° relative to the vertical.

The time taken for the strip to debond from the plate following the rupture of the adhesive joint under the effect of this stress is noted. This time is indicated in the table.

The corresponding results for a coating weight of 20 g/m² are shown in table 3.

Resistance Time of the Adhesive Joint to Static Shear at 90° C.:

The same test as before is performed on the adhesives but the test plate submitted to a weight of 1 kg is maintained at a temperature of 90° C.

The results for a coating weight of 20 g/m² are shown in table 3.

TABLE 3

| | Test results for a coating of 20 g/m² | | | | | | |
|---|---|---|---|---|---|---|---|
| | Peel 180° C. | | Loop tack | | Shear resistance at 90° C. | | Shear resistance at 23° C. |
| | (N/cm) | type of failure | (N/cm) | type of failure | time | type of failure | time |
| A | 5.91 | AF | 8.27 | AF | >24 h | | >24 h |
| 1 | 6.30 | AF | 11.02 | AF | >24 h | | >24 h |
| 2 | 0.94 | AF | 1.38 | AF | >24 h | | >24 h |
| 3 | 0.63 | AF | 2.13 | AF | 70 h | | 14 days |
| 4 | 2.95 | AF | 1.97 | AF | 45 h | | 18 days |
| 5 | 1.61 | AF | 3.98 | AF | 70 h | | 11 days |
| 6 | 2.36 | AF | 3.86 | AF | 70 h | | 8 days |
| 7 | 3.15 | AF | 3.35 | AF | 1 h | AF | 14 days |
| 9 | 6.69 | AF | 10.63 | AF | >24 h | | >24 h |
| 10 | 2.40 | AF | 4.13 | AF | 70 h | | 11 days |
| 11 | 1.57 | AF | 2.0 | AF | >20 min | AF | >4 h |
| 12 | 0.43 | AF | 1.42 | AF | >1 h | AF | 14 days |
| 13 | 0.53 | AF | 2.28 | AF | >1 h | | 14 days |
| 14 | 1.97 | AF | 2.76 | AF | 6 h | | >24 h |

AF = Adhesive Failure.

The invention claimed is:

1. A self-adhesive article comprising:
   a substrate having a Moisture-Vapour Transmission Rate superior or equal to 1000 g/m²/24 h, wherein at least one face of said substrate is coated with an adhesive layer obtained by curing an adhesive composition comprising at least one silyl-containing polymer, at least one compatible tackifying resin and at least one catalyst,
   said adhesive layer having a Moisture-Vapour Transmission Rate superior or equal to 300 g/m²/24 h for a coating weight below 50 g/m² and a Moisture-Vapour Transmission Rate superior or equal to 100 g/m²/24 h for a coating weight superior or equal to 50 g/m².

2. The self-adhesive article according to claim 1, wherein the adhesive layer having a coating weight below 50 g/m² has a Moisture-Vapour Transmission Rate superior or equal to 500 g/m²/24 h.

3. The self-adhesive article according to claim 1, wherein the adhesive layer having a coating weight superior or equal to 50 g/m² has a Moisture-Vapour Transmission Rate superior or equal to 200 g/m²/24 h.

4. The self-adhesive article according to claim 1, wherein the adhesive layer has a coating weight below 50 g/m² and has a Moisture-Vapour Transmission Rate superior to 500 g/m²/24 h.

5. The self-adhesive article according to claim 1, wherein the adhesive layer has a coating weight superior or equal to 50 g/m² and has a Moisture-Vapour Transmission Rate superior or equal to 400 g/m²/24 h.

6. The self-adhesive article according to claim 1, wherein said at least one silyl-containing polymer is obtained by the following process:
   a1) reacting a mixture of alcohols comprising a polyether polyol with a stoichiometric excess of diisocyanate, to form a polyurethane-polyether block having at least two terminal —NCO groups; and
   b1) reacting the product obtained from a1) with a stoichiometric quantity or slight stoichiometric excess quantity of an alpha, beta or gamma-aminosilane.

7. The self-adhesive article according to claim 1, wherein said at least one silyl-containing polymer is a silyl-containing polyurethane having polyurethane-polyether and polyurethane-polyester blocks, and said silyl-containing polyurethane is obtained by the following process:
   a2) reacting a mixture of alcohols comprising a polyether polyol with a stoichiometric excess of diisocyanate, in order to form a polyurethane-polyether block having at least two terminal —NCO groups;
   b2) reacting the product obtained from a2) with a stoichiometric excess of a polyester polyol, in order to form a polyurethane having polyurethane-polyether and polyurethane-polyester blocks comprising at least two terminal blocks consisting each in a polyurethane-polyester block having a terminal —OH group; and
   c2) reacting said polyurethane obtained from b2) with a stoichiometric quantity of an isocyanatosilane.

8. The self-adhesive article according to claim 1, wherein said tackifying resin is chosen from rosin ester resins and acrylic resins.

9. The self-adhesive article according to claim 1, wherein the adhesive composition comprises:
   a) from 20 to 85% by weight of at least one silyl-containing polymer;
   b) from 15 to 80% by weight of at least one tackifying resin; and
   c) from 0.01 to 3% by weight of at least one catalyst.

10. The self-adhesive article according to claim 1, wherein the tackifying resin has a softening point inferior or equal to 150° C.

11. The self-adhesive article according to claim 1, wherein the silyl-containing polymer is selected from the group consisting of a silyl-containing polyether, a silyl-containing polyurethane, a silyl-containing polyurethane having polyurethane-polyether and polyurethane-polyester blocks, and mixtures thereof.

12. The self-adhesive article according to claim 1, wherein the tackifying resin is selected from the group consisting of phenol modified terpene resins, hydrocarbon resins, rosin ester resins, acrylic resins and mixtures thereof.

13. A method for making the self-adhesive article of claim 1, comprising adhering the adhesive layer on the substrate.

14. The method according to claim 13, wherein the adhesive layer having a coating weight below 50 g/m² has a Moisture-Vapour Transmission Rate superior or equal to 500 g/m²/24 h.

15. The method according to claim 13, wherein the adhesive layer having a coating weight superior or equal to 50 g/m² has a Moisture-Vapour Transmission Rate superior or equal to 200 g/m²/24 h.

16. The method according to claim 13, wherein the substrate has a Moisture-Vapour Transmission Rate superior or equal to the Moisture-Vapour Transmission Rate of the adhesive layer.

17. A process for manufacturing the self-adhesive article according to claim 1, said process comprising:
   a) conditioning the adhesive composition at a temperature from 20° C. to 160° C.;
   b) coating the adhesive composition obtained from step a) onto a carrying surface;
   c) curing the coated adhesive composition by heating the carrying surface at a temperature from 20° C. to 200° C.; and
   d) laminating the cured adhesive layer onto the substrate having a Moisture-Vapour Transmission Rate superior or equal to 1000 g/m²/24 h.

18. The process according to claim 17, wherein said curing is carried out in an atmosphere in which from 5 to 100% of the molecules are water molecules.

* * * * *